US010285689B2

(12) United States Patent
Finley et al.

(10) Patent No.: US 10,285,689 B2
(45) Date of Patent: May 14, 2019

(54) ORTHOPEDIC IMPLANT FOR BONE FIXATION (71) Applicant: Biomet C.V., Gibraltar (GI)

(72) Inventors: Adam Finley, Winona Lake, IN (US); Jacy Hoeppner, Warsaw, IN (US); Kevin Stone, Winona Lake, IN (US); Brian Berelsman, Warsaw, IN (US)

(73) Assignee: Biomet C.V., Warsaw, IN (US)

(*) Notice: Subject to any disclaimer, the term of this patent is extended or adjusted under 35 U.S.C. 154(b) by 643 days.

(21) Appl. No.: 14/591,365

(22) Filed: Jan. 7, 2015

(65) Prior Publication Data
US 2016/0192930 A1    Jul. 7, 2016

(51) Int. Cl.
A61B 17/06    (2006.01)
A61B 17/064   (2006.01)
A61B 17/17    (2006.01)
A61B 17/15    (2006.01)

(52) U.S. Cl.
CPC .......... A61B 17/0642 (2013.01); A61B 17/15 (2013.01); A61B 17/17 (2013.01)

(58) Field of Classification Search
CPC ................................................ A61B 17/0642
See application file for complete search history.

(56) References Cited

U.S. PATENT DOCUMENTS

| 816,026 | A | | 3/1906 | Meier | |
|---|---|---|---|---|---|
| 4,454,875 | A | * | 6/1984 | Pratt | A61B 17/0642 606/219 |
| 4,474,514 | A | | 10/1984 | Jensen | |
| 4,548,202 | A | * | 10/1985 | Duncan | A61B 17/0643 606/220 |
| 4,719,917 | A | | 1/1988 | Barrows et al. | |
| 5,246,443 | A | | 9/1993 | Mai | |
| 5,788,698 | A | | 8/1998 | Savornin | |

(Continued)

FOREIGN PATENT DOCUMENTS

| CN | 107249478 A | 10/2017 |
|---|---|---|
| JP | 2018501019 A | 1/2018 |
| WO | WO-2016112173 A1 | 7/2016 |

OTHER PUBLICATIONS

"International Application Serial No. PCT/US2016/012452, International Search Report dated Mar. 29, 2016", 6 pgs.

(Continued)

Primary Examiner — Olivia C Chang
(74) Attorney, Agent, or Firm — Schwegman Lundberg & Woessner, P.A.

(57) ABSTRACT

A bone fixation device for use in fixation of a first and a second bone segment can include a first leg member, a second leg member and a lateral connecting portion. The first leg member can extend from a first originating end to a first distal end along a first longitudinal axis. The second leg member can extend from a second originating end to a second distal end along a second longitudinal axis. The lateral connecting portion can be integrally formed with the first and second leg members and connects the first and second leg members from the respective first and second originating ends. The lateral connecting portion can extend along a lateral body portion having a top portion that defines a lateral axis. At least one of the first and second longitudinal axes defines an obtuse angle with the lateral axis.

8 Claims, 6 Drawing Sheets (56) References Cited

U.S. PATENT DOCUMENTS

| | | | |
|---|---|---|---|
| 6,228,087 B1 | 5/2001 | Fenaroli et al. | |
| 6,325,805 B1 | 12/2001 | Ogilvie | |
| 6,783,531 B2 | 8/2004 | Allen | |
| 6,966,911 B2 | 11/2005 | Groiso | |
| 8,062,297 B2 | 11/2011 | Faillace | |
| 8,435,263 B2 | 5/2013 | Viola | |
| 8,679,123 B2 | 3/2014 | Kinmon | |
| 2006/0142771 A1 | 6/2006 | Beutter | |
| 2008/0161808 A1 | 7/2008 | Fox | |
| 2009/0087276 A1 | 4/2009 | Rose | |
| 2013/0150853 A1 | 6/2013 | Blacklidge | |
| 2017/0196604 A1* | 7/2017 | Hartdegen | A61B 17/0682 |

OTHER PUBLICATIONS

"International Application Serial No. PCT/US2016/012452, Written Opinion dated Mar. 29, 2016", 6 pgs.
"European Application Serial No. 16702458.7, Response filed Mar. 19, 2018 to Office Action dated Sep. 6, 2017", 15 pgs.

* cited by examiner

ORTHOPEDIC IMPLANT FOR BONE FIXATION

FIELD

The present disclosure relates generally to orthopedic implants and techniques and, more particularly, to fixation devices and techniques for correction, repair, reconstruction and/or fixation/fusion of bone segments.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Surgical procedures are often performed on a body, for example, a human body or anatomy, to repair, reconstruct and/or replace various portions thereof. For example, after trauma, there may be a need to fix bone segments together to immobilize the segments and permit healing. There may also be a need for fusion of bone segments or reconstruction of a bone or bone segments in connection with an osteotomy. Conventional implants that can be utilized in connection with such procedures do not provide optimal surfaces for bone in-growth and/or require separate, additional fixation systems, which require additional surgical instruments and procedures. Accordingly, there remains a need for improvement in the relevant art.

SUMMARY

This section provides a general summary of the disclosure, and is not a comprehensive disclosure of its full scope or all of its features.

A bone fixation device for use in fixation of a first and a second bone segment can include a first leg member, a second leg member and a lateral connecting portion. The first leg member can extend from a first originating end to a first distal end along a first longitudinal axis. The second leg member can extend from a second originating end to a second distal end along a second longitudinal axis. The lateral connecting portion can be integrally formed with the first and second leg members and connects the first and second leg members from the respective first and second originating ends. The lateral connecting portion can extend along a lateral body portion having a top portion that defines a lateral axis. At least one of the first and second longitudinal axes defines an obtuse angle with the lateral axis. Advancement of the bone fixation device into respective first and second bone segments urges the first and second bone segments toward each other as a result of the respective first and second leg members advancing into the respective first and second bone segments.

According to additional features, the first longitudinal axis and the lateral axis are perpendicular to each other. The first and second originating ends can be separated by an originating end distance. The first and second distal ends can be separated by a distal end distance. The distal end distance can be greater than the originating end distance. Both of the first and second longitudinal axes can define obtuse angles with the lateral axis.

According to other features, the bone fixation device can comprise a solid portion and a porous portion. The top surface portion can comprise the solid portion and includes a substantially smooth outer top surface. The first distal end and the second distal end can be formed by the solid portion. The lateral connecting portion can include a bottom surface portion having an arcuate profile. The lateral connecting portion, including the top surface portion, is configured to be implanted to a recessed position within the first and second bone segments.

The bone fixation device can further comprise a jig assembly configured to prepare the first and second bone segments for receipt of the bone fixation device. The jig assembly can comprise a jig body, a first peg member and a second peg member. The jig body can be configured to prepare a first hole in the first bone segment and a second hole in the second bone segment. The jig body can define first and second longitudinal openings connected by a connecting slot. The first peg member can have a first locating post at a distal end and a first lateral opening at a proximal end. The second peg member can have a second locating post at a distal end and a second lateral opening at a proximal end. The first and second longitudinal openings can be configured to initially receive a drill bit for preparation of respective holes in the first and second bone segments. Subsequently, the first and second longitudinal openings are configured to receive the first and second locating posts of the first and second peg members such that the first and second lateral openings align for receipt of a cutting tool for preparation of a lateral opening configured for receipt of the lateral connecting portion.

A bone fixation device constructed in accordance to additional features of the present disclosure used for fixation of a first and second bone segment can include a first leg member, a second leg member and a lateral connecting portion. The first leg member can extend from a first originating end to a first distal end along a first longitudinal axis. The first leg member can have a first cross-sectional profile. The second leg member can extend from a second originating end to a second distal end along a second longitudinal axis. The second leg member can have a second cross-sectional profile. The lateral connecting portion can be integrally formed by the first and second leg members and connects the first and second leg members from the respective first and second originating ends. The lateral connecting portion can extend along a lateral body portion having a top surface portion that defines a lateral axis. At least one of the first and second leg members tapers from the respective originating end to the respective distal end. Advancement of the bone fixation device into respective first and second bone segments urges the first and second bone segments toward each other as a result of the respective first and second leg members advancing into the respective first and second bone segments.

According to other features, the bone fixation device comprises a solid portion and a porous portion. The top surface portion can comprise the solid portion and includes a substantially smooth outer surface. The first distal end and the second distal end are formed by the solid portion. The lateral connecting portion can include a bottom surface portion having an arcuate profile.

A method for fixing a first bone segment relative to a second bone segment according to the present disclosure includes preparing a first opening in the first bone segment. A second opening can be prepared in the second bone segment. A bone fixation device can be inserted into the first and second bone segments. The bone fixation device can include (i) a first leg member that extends from a first originating end to a first distal end along a first longitudinal axis, (ii) a second leg member that extends from a first originating end to a second distal end along a second longitudinal axis, and (iii) a lateral connecting portion that is integrally formed with the first and second leg members and connects the first and second leg members from the respective first and second originating ends. The lateral connecting portion can extend along a lateral body portion having a top surface that defines a lateral axis. At least one of the first and second longitudinal axes defines an obtuse angle with the lateral axis. The first leg member is further advanced into the first opening and the second leg member is further advanced into the second opening. Advancement of the bone fixation device into the respective first and second bone segments urges the first and second bone segments toward each other as a result of the respective first and second leg members advancing into the respective first and second openings.

According to additional features, the method can further include locating a jig body relative to the first and second bone segments. The jig body can define first and second longitudinal openings connected by a connecting slot. The jig body can be configured to guide a drill bit during preparation of the first opening in the first bone segment and the second opening in the second bone segment. The drill bit can be advanced through the first longitudinal opening creating the first opening in the first bone segment. The drill bit can be further advanced through the second longitudinal opening creating the second opening in the second bone segment. Subsequent to preparation of the first and second openings, the method can include locating a first locating post on a first peg member into the first longitudinal opening. A second locating post on a second peg member can be located into the second longitudinal opening. A first lateral opening on the first peg member can be aligned with a second lateral opening on the second peg member. A lateral cutting member can be guided through the connecting slot, the first lateral opening and the second lateral opening while creating a connecting slot in the first and second bone segments for receipt of the lateral connecting portion of the bone fixation device.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

DETAILED DESCRIPTION

The following description is merely exemplary in nature and is not intended to limit the present disclosure, its application, or uses. Examples are provided so that this disclosure will be thorough, and will fully convey the scope to those who are skilled in the art. Numerous specific details are set forth such as examples of specific components, devices, systems and/or methods, to provide a thorough understanding of the present disclosure. It will be apparent to those skilled in the art that specific details need not be employed, that examples shown herein may be embodied in many different forms and that neither should be construed to limit the scope of the disclosure.

The present teachings provide bone fixation devices and methods for using the same to facilitate bone fixation and healing. In an exemplary aspect, the bone fixation devices can be utilized for fracture fixation, fusion of two adjacent bone segments (e.g., joint fusion), and/or for stabilization/reconstruction of a bone or bone segments, including in connection with an osteotomy or the like. In this regard, the devices discussed herein will be referred to as fixation devices and it will be understood that such fixation devices can perform a stabilization function as well as a fixation function between bone segments, a fusion function between bone segments and/or reconstruction of a bone or bone segments. As used herein, "bone segments" can refer to two segments of the same bone (e.g., relative to a fracture line or osteotomy) or adjacent bones (e.g., of a joint). Further, the discussion herein can be utilized for fixation, fusion and/or reconstruction/repair of various different small bones and/or joints, such as in the hand or foot or elsewhere in the anatomy.

Figure 1:
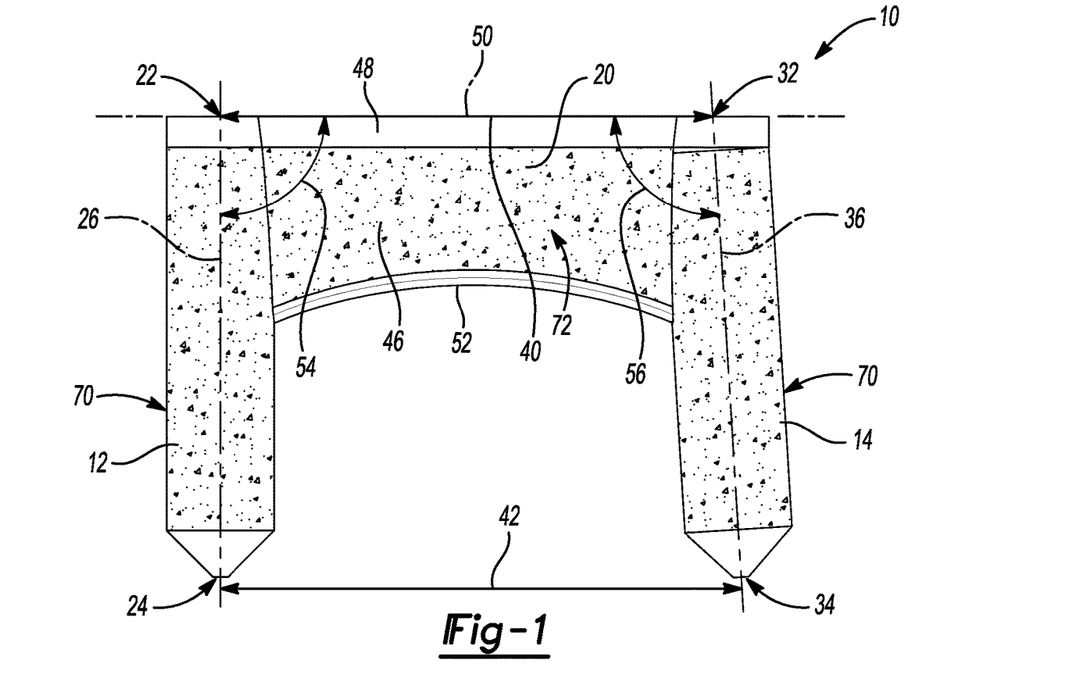
FIG. 1 is a front view of an exemplary bone fixation device in accordance with various aspects of the present disclosure.
Figure 2:
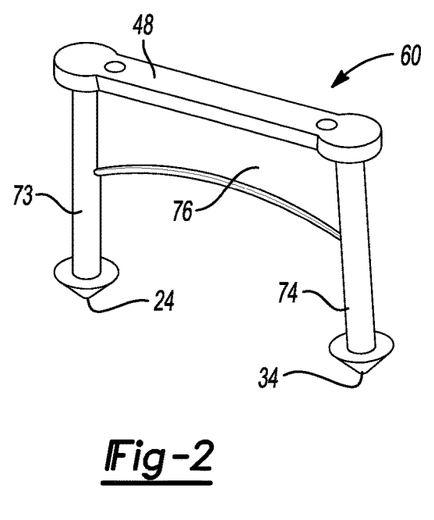
FIG. 2 is a perspective view of an exemplary core portion of the bone fixation device of FIG. 1 in accordance with various aspects of the present disclosure.
Figure 3:
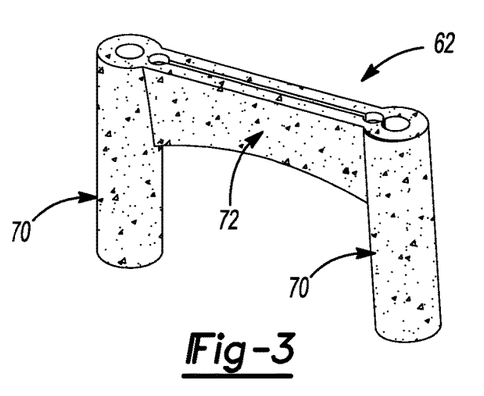
FIG. 3 is a perspective view of an exemplary porous metal portion or construct of the bone fixation device of FIG. 1 in accordance with various aspects of the present disclosure.

With initial reference to FIGS. 1-3, an exemplary bone fixation device according to various aspects of the present teachings is shown and generally identified at reference numeral 10. As will be discussed in greater detail below, the bone fixation device 10 can, in one exemplary implementation, provide for stabilization of bone segments, such as the Talus and Navicular bones of the Talo-Navicular joint, as well as fixation of the bones with a single, unitary structure. In one exemplary aspect, the bone fixation device 10 can include a pair of legs in spaced relation to each other that are integrally formed with and connected by a lateral connecting portion. As will also be discussed in greater detail below, the bone fixation device 10 is in the general shape of a staple and can include a solid metal portion and a porous metal portion or region.

The bone fixation device 10 can include a first leg member 12, a second leg member 14 and a lateral connecting portion 20. The lateral connecting portion 20 can be integrally formed with the first and second leg members 12 and 14. As will become appreciated from the following discussion one or both of the leg members 12 and 14 can extend at an obtuse angle relative to the lateral connecting portion 20. The resulting geometry can urge respective first and second bone segments toward each other as a result of the respective first and second leg members 12 and 14 advancing into the respective first and second bone segments as will be described in detail with respect to FIGS. 9 and 10.

The first leg member 12 can extend from a first originating end 22 to a first distal end 24 along a first longitudinal axis 26. The second leg member 14 can extend from a second originating end 32 to a second distal end 34 along a second longitudinal axis 36. The first and second originating ends 22 and 32 can be separated by an originating end distance 40. The first and second distal ends 24, 34 can be separated by a distal end distance 42. The distal end distance 42 is greater than the originating end distance 40.

The lateral connecting portion 20 can connect the first and second leg members 12 and 14 from the respective first and second originating ends 22 and 32. The lateral connecting portion 20 can extend along a lateral body portion 46 having a top surface portion 48 that defines a lateral axis 50. The lateral connecting portion 20 can further include a bottom surface portion 52 having an arcuate profile. The lateral connecting portion 20 is configured to be inserted into the bone. In the example shown in FIG. 1, the first axis 26 and the lateral axis 50 define an angle 54. The angle 54 is a right angle. In this regard, the first axis 26 and the lateral axis 50 are perpendicular relative to each other. The second axis 36 and the lateral axis 50 define an angle 56. The angle 56 is an obtuse angle. The angle 56 can generally define any angle greater than 90 degrees. It is contemplated that a kit of bone fixation devices 10 may be provided having leg members that include various angles wherein a surgeon may select an appropriate bone fixation device for a given patient.

In one exemplary implementation, the bone fixation device 10 can be formed using an additive manufacturing process with a titanium alloy core portion 60 (FIG. 2) and a porous metal titanium alloy portion 62 (FIG. 3). It will be appreciated that while the titanium alloy core portion 60 and the porous metal titanium alloy portion 62 are shown in FIGS. 2 and 3 as distinct constructs, they are formed as a unitary piece. In this regard, they are shown as stand-alone constructs merely for illustrative purposes.

In one configuration, the distal ends 24 and 34 of the first and second leg members 12 and 14, and the upper surface portion 48 of the lateral body portion 46 can be formed of the titanium allow core portion 60. In this way the distal ends 24 and 34 and the upper surface portion 48 can have a smooth or substantially smooth outer surface. Outer surfaces 70 of the first and second leg members 12 and 14 and outer surfaces 72 of the lateral body portion 46 can be formed as a porous metal construct or structure.

In another exemplary implementation, the top surface portion 48 and bottom surface portion 52 can be formed of solid or substantially solid titanium alloy having a smooth or substantially smooth outer surface, as shown for example in FIG. 1. Additionally, the leading edge of the bone fixation device 10, namely the bottom surface portion 52, can be formed from the solid metal alloy with a smooth outer surface to aid with insertion into bone.

In this exemplary implementation, the porous metal portion 62 can be formed from a titanium alloy using an additive manufacturing process, such as with OsseoTi™, which is commercially available from Biomet Manufacturing, LLC (Warsaw, Ind., USA). Briefly, however, OsseoTi is highly biocompatible, has high corrosion resistance and includes a highly interconnected porous architecture that mimics the porous structure of human cancellous bone, which can enhance bone integration and in-growth. In one exemplary implementation, the OsseoTi porous metal construct can include a porosity of approximately 70%.

With particular reference to FIGS. 2 and 3, in one exemplary implementation, the solid portion 60 can be formed with the additive manufacturing process from the same titanium alloy as the OsseoTi porous metal construct that forms the above-discussed porous metal portion 62. In the exemplary implementation illustrated, the solid portion 60 can include the top surface 48 distal ends 24 and 34 as well as a first leg core 73, a second leg core 74 and a connecting portion core 76 formed as a continuous structure, FIG. 3 illustrates the porous metal portion 62 that surrounds the solid portion 60 except for at the areas identified above. The porous metal portion 62 can facilitate boney ingrowth of the surrounding bone of the first and second bone segments as will become appreciated herein.

Figure 4:
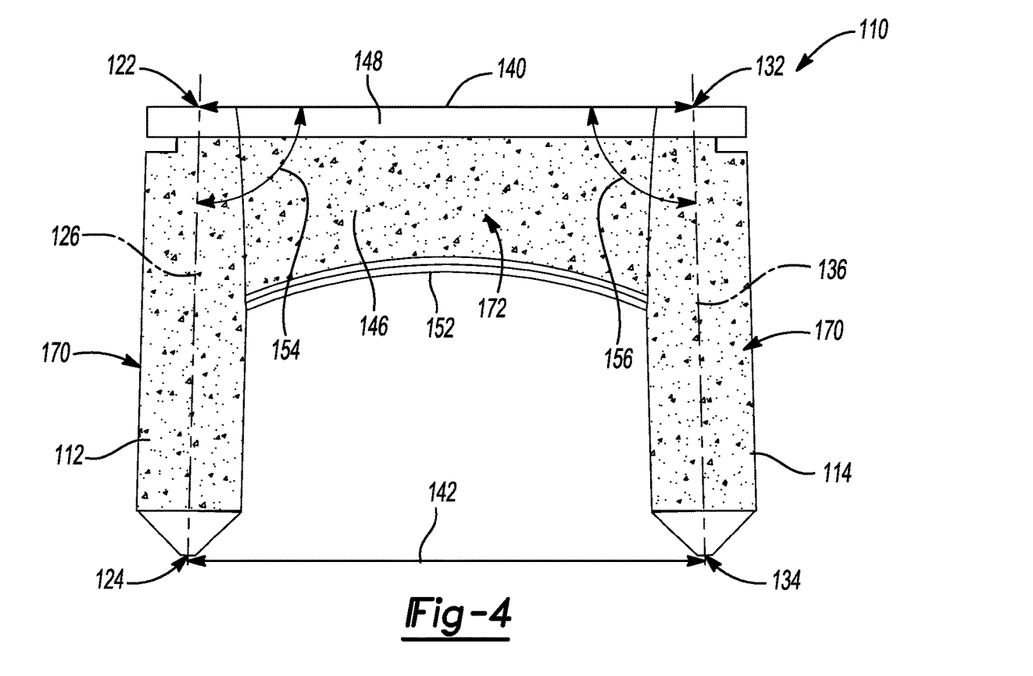
FIG. 4 is a front view of an exemplary bone fixation device constructed in accordance with another example of the present disclosure.
Figure 5:
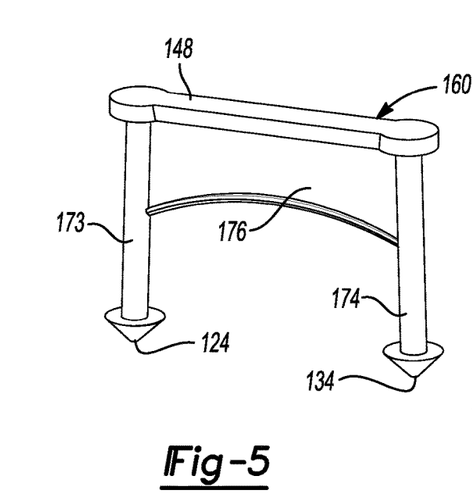
FIG. 5 is a perspective view of an exemplary core portion of the bone fixation device of FIG. 4 in accordance with various aspects of the present disclosure.
Figure 6:
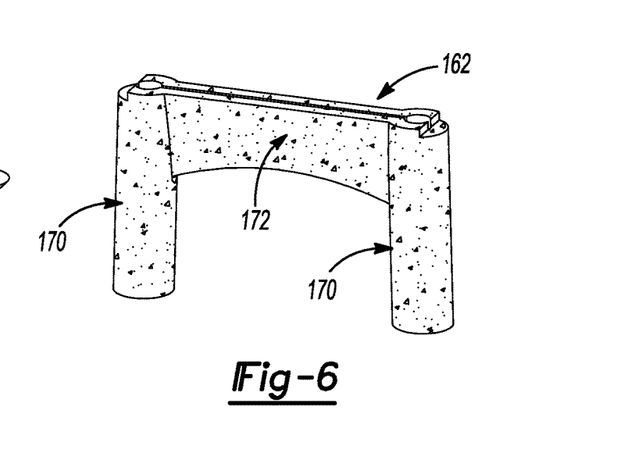
FIG. 6 is a perspective view of an exemplary porous metal portion or construct of the bone fixation device of FIG. 4 in accordance with various aspects of the present disclosure.

With reference now to FIGS. 4-6, an exemplary bone fixation device according to additional aspects of the present teachings is shown and generally identified at reference numeral 110. In one exemplary aspect, the bone fixation device 110 can include a pair of legs in spaced relation to each other that are integrally formed with and connected by a lateral connecting portion. The bone fixation device 110 is similar to the bone fixation device 10 however the bone fixation device 110 has legs that both extend at obtuse angles relative to the lateral connecting device. As will also be discussed in greater detail below, the bone fixation device 10 is in the general shape of a staple and can include a solid metal portion and a porous metal portion or region.

The bone fixation device 110 can include a first leg member 112, a second leg member 114 and a lateral connecting portion 120. The lateral connecting portion 120 can be integrally formed with the first and second leg members 112 and 114. Both of the leg members 112 and 114 can extend at an obtuse angle relative to the lateral connecting portion 120. The resulting geometry can urge respective first and second bone segments toward each other as a result of the respective first and second leg members 112 and 114 advancing into the respective first and second bone segments.

The first leg member 112 can extend from a first originating end 122 to a first distal end 124 along a first longitudinal axis 126. The second leg member 114 can extend from a second originating end 132 to a second distal end 134 along a second longitudinal axis 136. The first and second originating ends 122 and 132 can be separated by an originating end distance 140. The first and second distal ends 124, 134 can be separated by a distal end distance 142. The distal end distance 142 is greater than the originating end distance 140.

The lateral connecting portion 120 can connect the first and second leg members 112 and 114 from the respective first and second originating ends 122 and 132. The lateral connecting portion 120 can extend along a lateral body portion 146 having a top surface portion 148 that defines a lateral axis 150. The lateral connecting portion 120 can further include a bottom surface portion 152 having an arcuate profile. In the example shown in FIG. 4, the first axis 126 and the lateral axis 150 define an angle 154. The angle 154 is an obtuse angle. The second axis 136 and the lateral axis 150 define an angle 156. The angle 156 is an obtuse angle. The angles 154 and 156 can both generally define any angle greater than 90 degrees. The angles 154 and 156 can be equivalent or distinct to each other. It is contemplated that a kit of bone fixation devices 110 may be provided having leg members that include various angles wherein a surgeon may select an appropriate bone fixation device for a given patient. Moreover, a kit having varieties of both of the bone fixation devices 10 and 110 is contemplated.

In one exemplary implementation, the bone fixation device 110 can be formed using an additive manufacturing process with a titanium alloy core portion 160 (FIG. 5) and a porous metal titanium alloy portion 162 (FIG. 6). It will be appreciated that while the titanium alloy core portion 160 and the porous metal titanium alloy portion 162 are shown in FIGS. 5 and 6 as distinct constructs, they are formed as a unitary piece. In this regard, they are shown as stand-alone constructs merely for illustrative purposes.

In one configuration, the distal ends 124 and 134 of the first and second leg members 112 and 114, and the upper surface portion 148 of the lateral body portion 146 can be formed of the titanium allow core portion 160. In this way the distal ends 124 and 134 and the upper surface portion 148 can have a smooth or substantially smooth outer surface. Outer surfaces 170 of the first and second leg members 112 and 114 and outer surfaces 172 of the lateral body portion 146 can be formed as a porous metal construct or structure.

In another exemplary implementation, the top surface portion 148 and bottom surface portion 152 can be formed of solid or substantially solid titanium ahoy having a smooth or substantially smooth outer surface, as shown for example in FIG. 4. Additionally, the leading edge of the bone fixation device 110, namely the bottom surface portion 152, can be formed from the solid metal alloy with a smooth outer surface to aid with insertion into bone. In this exemplary implementation, the porous metal portion 162 can be a formed from a titanium alloy using an additive manufacturing process such as described above. In addition, the solid portion 160 can also be formed with the additive manufacturing process described above. In the exemplary implementation illustrated, the solid portion 160 can include the top surface 148, distal ends 124 and 134 as well as a first leg core 173, a second leg core 174 and a connect g portion core 176 formed as a continuous structure. FIG. 6 illustrates the porous metal portion 162 that surrounds the solid portion 160 except for at the areas identified above. The porous metal portion 162 can facilitate boney ingrowth of the surrounding bone of the first and second bone segments as will become appreciated herein.

Figure 7:
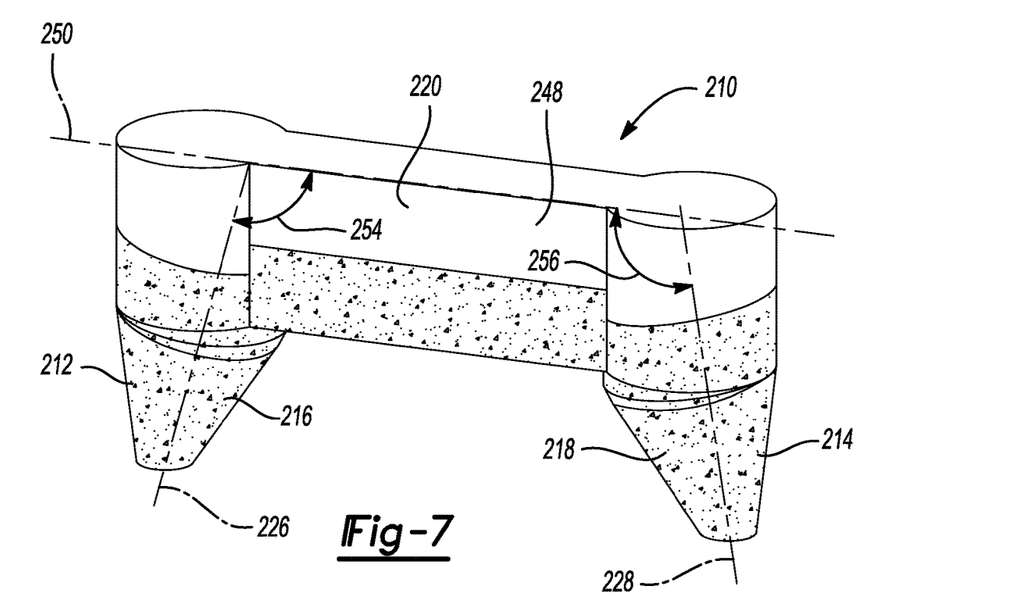
FIG. 7 is a perspective view of another bone fixation device constructed in accordance to additional features of the present disclosure.
Figure 8:
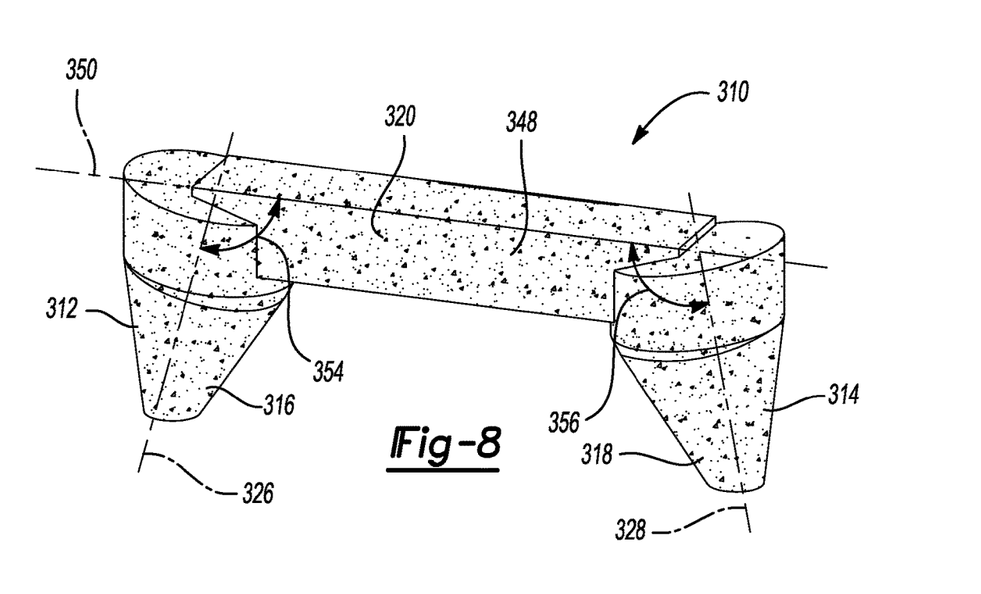
FIG. 8 is a perspective view of yet another bone fixation device constructed in accordance to other features of the present disclosure.

Turning now to FIGS. 7 and 8 additional examples of the present disclosure are shown. A bone fixation device 210 is shown in FIG. 7 having a first leg member 212, a second leg member 214 and a lateral connecting portion 220. The lateral connecting portion 220 can be integrally formed with the first and second leg members 212 and 214. In the example shown, the first and second leg members 212, 214 can define conical portions 216 and 218 that define respective axes 226 and 228. The axis 226 can define an angle 254 relative to a lateral axis 250 extending along the lateral connecting portion 220. The angle 254 can be obtuse. The axis 228 can define an angle 256 relative to the lateral axis 250. The angle 256 can be obtuse. The geometry of the first and second leg members 212, 214 can urge respective bone members toward each other during fixation similar to the other bone fixation devices described herein. The bone fixation device 210 has portions formed of solid material and portions formed of porous material. Specifically, the bone fixation device 210 includes a solid upper surface portion 248. It will be appreciated that the solid and porous material may be arranged differently.

FIG. 8 illustrates a bone fixation device 310 having a first leg member 312, a second leg member 314 and a lateral connecting portion 320. The lateral connecting portion 320 can be integrally formed with the first and second leg members 312 and 314. In the example shown, the first and second leg members 312, 314 can define conical portions 316 and 318 that define respective axes 326 and 328. The axis 326 can define an angle 354 relative to a lateral axis 350 extending along the lateral connecting portion 320. The angle 354 can be obtuse. The axis 328 can define an angle 356 relative to the lateral axis 350. The angle 356 can be obtuse. The geometry of the first and second leg members 312, 314 can urge respective bone members toward each other during fixation similar to the other bone fixation devices described herein. While the bone fixation device 310 is shown formed entirely of porous material, other configurations are contemplated. In this regard, the bone fixation device 310 may additionally include a solid metal core or other portions thereof.

The bone fixation devices 210 and 310 are shown in FIGS. 7 and 8 to illustrate that the constructs may be arranged in any manner having various solid portions and porous portions. In this regard, the leg members may be arranged having various heights and various angles relative to the connecting portion as needed for a particular patient.

Figure 11:
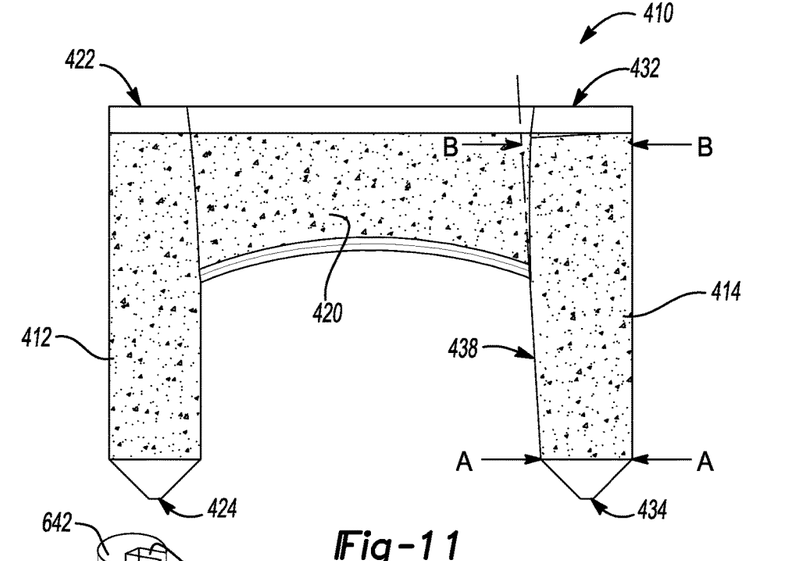
FIG. 11 is a perspective view of an exemplary bone fixation device constructed in accordance to additional features of the present disclosure.

With reference now to FIG. 11, a bone fixation device 410 constructed in accordance to additional features will be described. The bone fixation device 410 can include a first leg member 412, a second leg member 414 and a lateral connecting portion 420. The lateral connecting portion 420 can be integrally formed with the first and second leg members 412 and 414. As will become appreciated from the following discussion, the second leg member 414 according to the example shown tapers toward a distal end. The tapered geometry will urge respective bone segments toward each other as a result of the respective first and second leg members 412 and 414 advancing into respective bone segments. The cross-section of the second leg member 414 can be partially or entirely conical and/or oblong. Other geometries are contemplated that result in a bone engaging surface 438 that tapers toward the second distal end 434.

The first leg member 412 can extend from a first originating end 422 to a first distal end 424. The second leg member 414 can extend from a second originating end 432 to a second distal end 434. The second leg member 414 can have a first width A-A at the second distal end 434 and a second width B-B at the second originating end 432. The first width A-A can be smaller than the second width B-B. In this regard, as a bone engaging surface 438 slidably negotiates along a corresponding bone, the tapered nature will cause the bone segments to move toward each other as the bone fixation device 410 is advanced into the bone.

With general reference now to FIGS. 9, 10, 12 and 13, an exemplary surgical method for fixing two adjacent bone segments 502 and 504 will be described according to one example of the present disclosure. The bone fixation device 10 can be utilized in various surgical techniques, such as for fracture fixation, fixation of two adjacent bone segments (e.g., joint fusion), and/or for stabilization/reconstruction of a bone or bone segments, including in connection with an osteotomy or the like.

Figure 9:
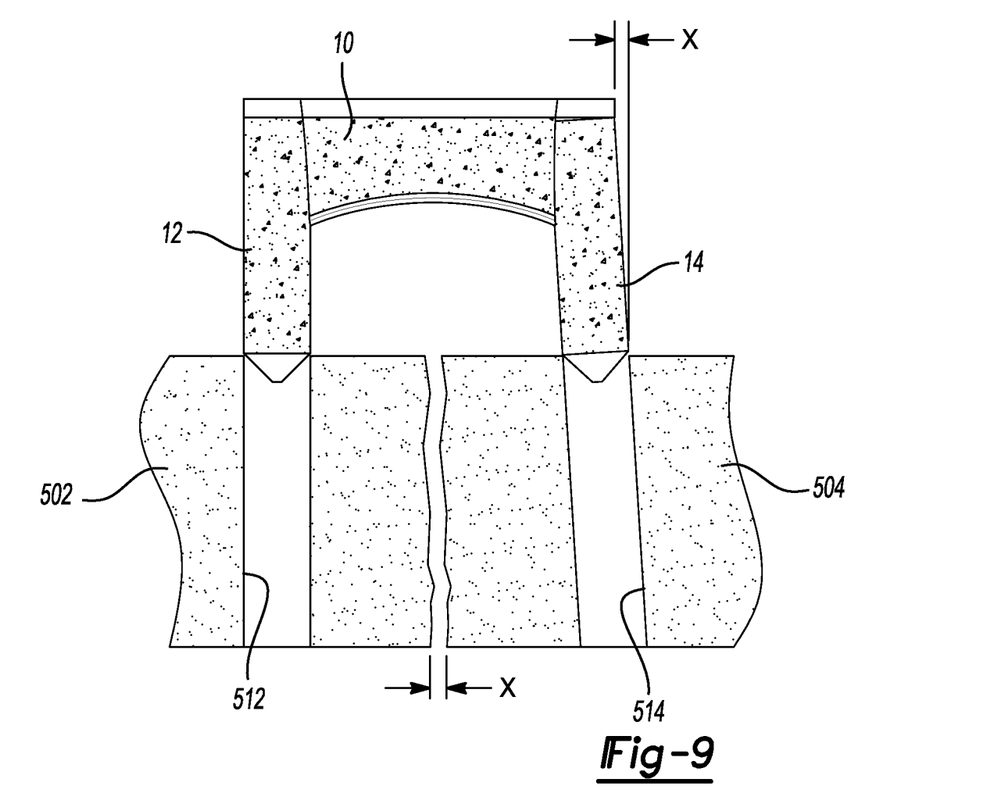
FIGS. 9 and 10 are exemplary sequence views of the bone fixation device of FIG. 1 being implanted into a first and second bone segment according to one example of the present disclosure.
Figure 10:
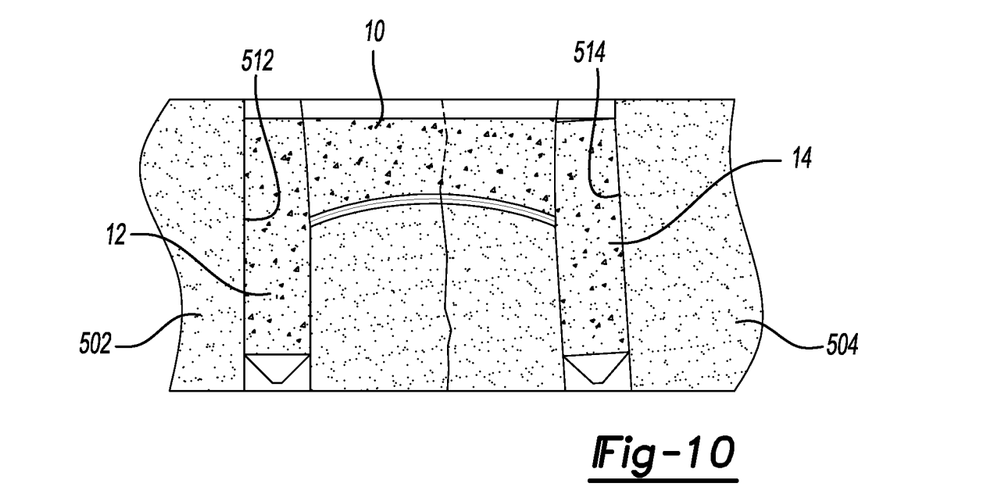

With initial reference to FIGS. 9 and 10, the bone segments 502 and 504 can be prepped for implantation of the bone fixation device 10. A first bone hole or opening 512 and a second bone hole or opening 514 can be created in the respective first and second bone segments 502 and 504 for receipt of the first and second leg members 12 and 14. In one example, the second bone hole 514 can be formed at an angle corresponding or substantially corresponding to the angle 56 defined between the second longitudinal axis 36 of the second leg 14 and the lateral axis 50 of the lateral connecting portion 20 (see also FIG. 1). A portion of the bone can also be removed for receipt of the lateral connecting portion 20. In the implanted position (FIG. 10), the lateral connecting portion 20, including the top surface portion 148, is configured to be implanted to a recessed position within the first and second bone segments 502, 504.

As the first and second leg members 12 and 14 of the bone fixation device 10 are advanced into the respective bone holes 512 and 514, the angled relationship of the second leg 14 (identified by a distance "X") will draw the two bone segments 502 and 504 toward each other (the same distance "X") from a position shown in FIG. 9 to a position shown in FIG. 10. In this regard, the fracture that separates the bone segments 502 and 504 is forced together as the angled leg member 14 advances along the bone hole 514. The bone fixation device 10 also creates compression across the joint/fracture as it is inserted which decreases the amount of preparation work needed to "pre-compress" the joint/fracture before implanting the bone fixation device 10. Moreover, micro-motion can be reduced between the first and second bone segments 502 and 504 earner than prior art devices encouraging early bone in-growth to allow a patient to return to normal activities in shorter recovery times. It will be appreciated that a similar result may be realized using the bone fixation device 110 where angled bone holes are prepared and the bone segments are drawn toward each other upon advancement of the bone fixation device 110 into the bone segments.

Figure 12:
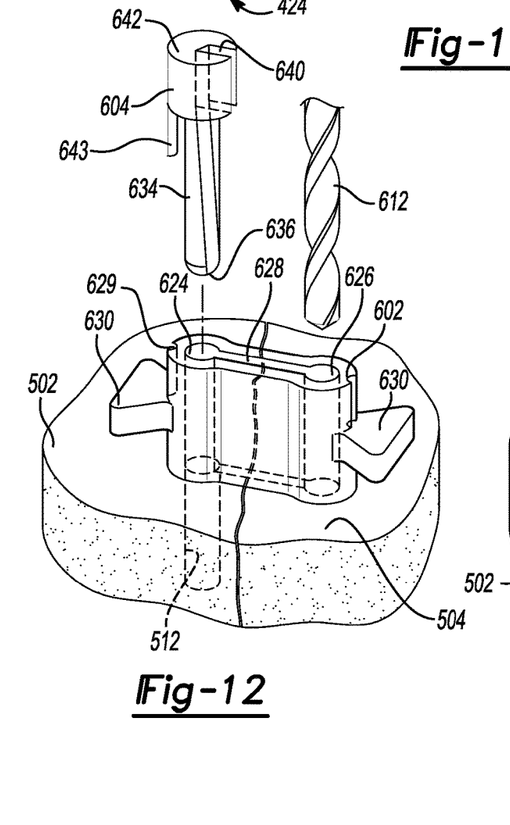
FIGS. 12 and 13 are exemplary sequence views of an exemplary jig assembly being used to prepare the first and second bone segments for receipt of the bone fixation device of FIG. 1.
Figure 13:
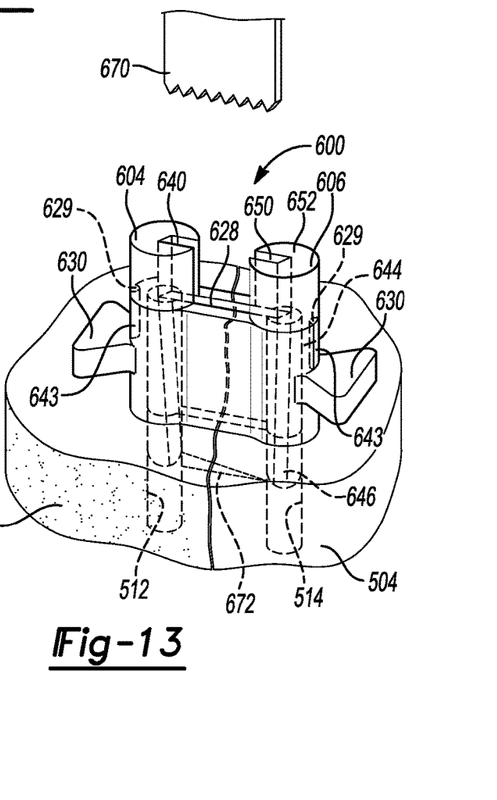
Figure 14A:
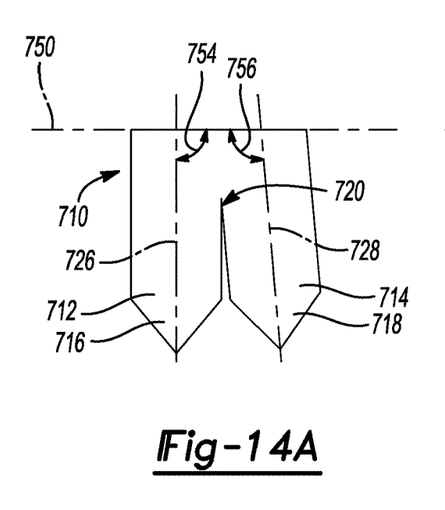
FIG. 14A is a side view of yet another bone fixation device constructed in accordance to other features of the present disclosure.
Figure 14B:
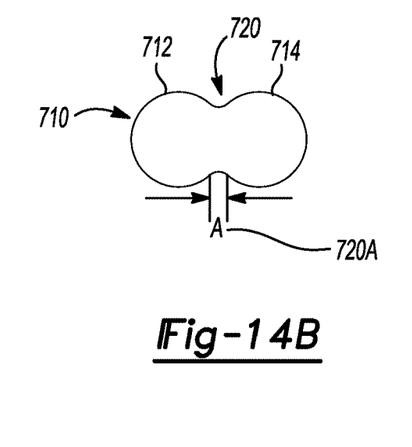
FIG. 14B is a top view of the bone fixation device of FIG. 14A.

With reference now to FIGS. 12 and 13, a jig assembly 600 constructed in accordance with the present disclosure and configured to prepare the first and second bone segments 502 and 504 will be described. The jig assembly 600 generally includes a jig body 602, a first peg member 604 and a second peg member 606. The jig body 602 can be configured to guide a cutting tool or drill bit 612 through a first opening 624 and a second opening 626. A connecting slot 628 can be formed through the jig body 602 and connects the first and second openings 624 and 626. An anti-rotation slot 629 can be defined in the jig body 602. The jig body 602 can include a pair of outwardly extending grasping portions 630.

The first peg member 604 can have a first locating post 634 at a distal end 636 and a first lateral opening 640 at a proximal end 642. The first lateral opening 640 can also extend along a portion of the first locating post 634. The lateral opening 640 can be tapered or straight. An anti-rotation peg 643 can extend from the proximal end 642. The anti-rotation peg 643 can be configured to be received by the anti-rotation slot 629. The anti-rotation peg 643 and anti-rotation slot 629 cooperate to inhibit rotation of the first peg member 604 around its longitudinal axis. The second peg member 606 can have a second locating post 644 at a distal end 646 and a second lateral opening 650 at a proximal end 652.

Once the drill bit 612 has created the first and second bone holes 512 and 514, the first locating post 634 can be inserted into the first bone hole 512 and the second locating post 644 can be inserted into the second bone hole 514. It will be appreciated that subsequent to one of the bone holes 512 or 514 being prepared, the corresponding first and second peg member 604 or 606 may be inserted to further secure the jig body 602 relative to the bone segments 502, 504. Additionally or alternatively, the jig body 602 may be pinned to the first and second bone segments 502 and 504 prior to drilling with the drill bit 612. In some examples, the jig body 602 may be pinned through the grasping portions 630. The first and second peg members 604 and 606 can be rotated such that the first and second lateral openings 640 and 650 align for receipt of a lateral cutting tool 670 for preparation of a lateral opening or connecting slot 672 configured for receipt of the lateral connecting portion 20.

With reference now to FIGS. 14A-16B, additional bone fixation devices constructed in accordance to other features of the present example will be described. With initial reference to FIGS. 14A and 14B, a bone fixation device 710 includes a first leg member 712, a second leg member 714 and a lateral connecting portion 720. The lateral connecting portion 720 can be integrally formed with the first and second leg members 712 and 714. The lateral connecting portion 720 can extend a distance 720A between the first and second leg members 712 and 714. In the example shown, the first and second leg members 712 and 714 can be cylindrical portions 716 and 718 that define respective axes 726 and 728. The axis 726 can define an angle 754 relative to a lateral axis 750 extending along the lateral connecting portion 720. The angle 754 can be a right angle. The axis 728 can define an angle 756 relative to the lateral axis 750. The angle 756 can be obtuse. In other examples, both of the angles 754 and 756 can be obtuse.

Figure 15A:
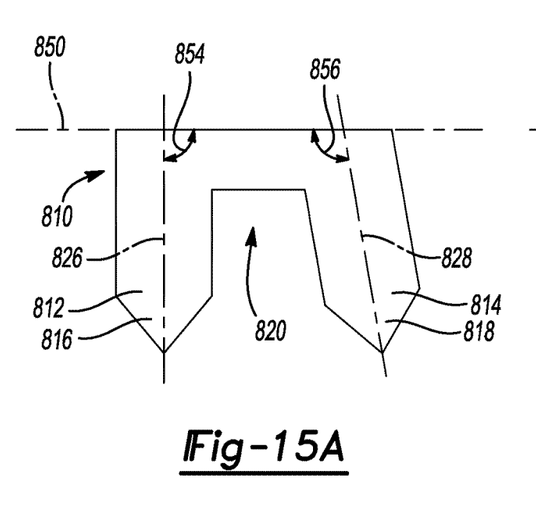
FIG. 15A is a side view of another bone fixation device constructed in accordance to other features of the present disclosure.
Figure 15B:
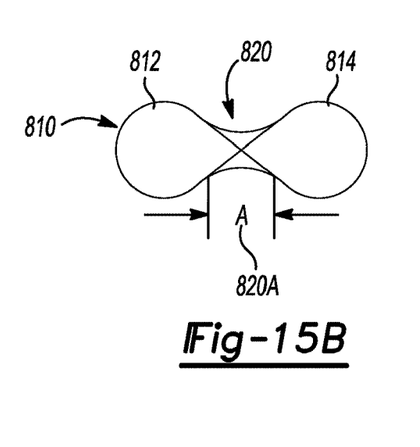
FIG. 15B is a top view of the bone fixation device of FIG. 15A.

With reference now to FIGS. 15A and 15B, a bone fixation device 810 includes a first leg member 812, a second leg member 814 and a lateral connecting portion 820. The lateral connecting portion 820 can be integrally formed with the first and second leg members 812 and 814. The lateral connecting portion 820 can extend a distance 820A between the first and second leg members 812 and 814. In the example shown, the first and second leg members 812 and 814 can be cylindrical, oblong or oval portions 816 and 818 that define respective axes 826 and 828. The axis 826 can define an angle 854 relative to a lateral axis 850 extending along the lateral connecting portion 820. The angle 854 can be a right angle. The axis 828 can define an angle 856 relative to the lateral axis 850. The angle 856 can be obtuse. In other examples, both of the angles 854 and 856 can be obtuse.

Figure 16A:
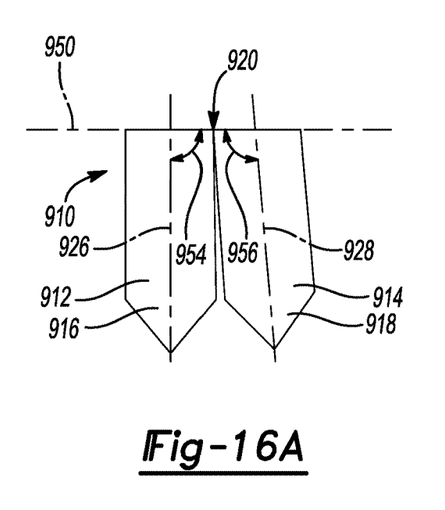
FIG. 16A is a side view of another bone fixation device constructed in accordance to other features of the present disclosure.
Figure 16B:
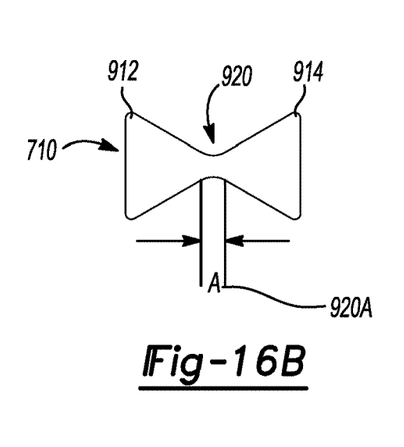
FIG. 16B is a top view of the bone fixation device of FIG. 16A.

With reference now to FIGS. 16A and 16B, a bone fixation device 910 includes a first leg member 912, a second leg member 914 and a lateral connecting portion 920. The lateral connecting portion 920 can be integrally formed with the first and second leg members 912 and 914. The lateral connecting portion 920 can extend a distance 920A between the first and second leg members 912 and 914. In the example shown, the first and second leg members 912 and 914 can be triangular cross-sectional portions 916 and 918 that define respective axes 926 and 928. The axis 926 can define an angle 954 relative to a lateral axis 950 extending along the lateral connecting portion 920. The angle 954 can be a right angle. The axis 928 can define an angle 956 relative to the lateral axis 950. The angle 956 can be obtuse. In other examples, both of the angles 954 and 956 can be obtuse.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A bone fixation system comprising:
   a bone fixation device for use in fixation of a first and a second bone segment, the bone fixation device including:
   a first leg member that extends from a first originating end to a first distal end along a first longitudinal axis;
   a second leg member that extends from a second originating end to a second distal end along a second longitudinal axis;
   a lateral connecting portion that is integrally formed with the first and second leg members and connects the first and second leg members from the respective first and second originating ends, the lateral connecting portion extending along a lateral body portion having a top surface portion that defines a lateral axis; and
   wherein at least one of the first and second longitudinal axes defines an obtuse angle with the lateral axis and wherein advancement of the bone fixation device into respective first and second bone segments urges the first and second bone segments toward each other as a result of the respective first and second leg members advancing into the respective first and second bone segments; and
   a jig assembly configured to prepare the first and second bone segments for receipt of the bone fixation device, the jig assembly comprising:
   a jig body configured to prepare a first hole in the first bone segment and a second hole in the second bone segment, the jig body defining first and second longitudinal openings connected by a connecting slot;
   a first peg member having a first locating post at a distal end and a first lateral opening at a proximal end;
   a second peg member having a second locating post at a distal end and a second lateral opening at a proximal end; and
   wherein the first and second longitudinal openings are configured to initially receive a drill bit for preparation of respective holes in the first and second bone segments and subsequently receive the first and second locating posts of the first and second peg members such that the first and second lateral openings align for receipt of a cutting tool for preparation of a lateral opening configured for receipt of the lateral connecting portion.

2. The bone fixation system of claim 1, wherein the other one of the first longitudinal axis or the second longitudinal axis is perpendicular to the lateral axis.

3. The bone fixation system of claim 1, wherein the first and second originating ends are separated by an originating end distance and wherein the first and second distal ends are separated by a distal end distance, wherein the distal end distance is greater than the originating end distance.

4. The bone fixation system of claim 1, wherein the bone fixation device comprises a solid portion and a porous portion.

5. The bone fixation system of claim 4 wherein the top surface portion comprises the solid portion and includes a smooth outer surface.

6. The bone fixation system of claim 5 wherein the first and second distal ends are formed by the solid portion.

7. The bone fixation system of claim 6 wherein the lateral connecting portion includes a bottom surface portion having an arcuate profile.

8. The bone fixation system of claim 7 wherein the lateral connecting portion, including the top surface portion, is configured to be implanted to a recessed position within the first and second bone segments.

* * * * *